(12) United States Patent
Shoji et al.

(10) Patent No.: US 7,025,876 B2
(45) Date of Patent: Apr. 11, 2006

(54) SAMPLE PROCESSING DEVICE AND SAMPLE PROCESSING METHOD

(75) Inventors: Yoshiyuki Shoji, Mito (JP); Toshiaki Yokobayashi, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 127 days.

(21) Appl. No.: 10/486,337

(22) PCT Filed: Sep. 17, 2001

(86) PCT No.: PCT/JP01/08062

§ 371 (c)(1),
(2), (4) Date: Feb. 10, 2004

(87) PCT Pub. No.: WO03/025170

PCT Pub. Date: Mar. 27, 2003

(65) Prior Publication Data

US 2004/0181050 A1    Sep. 16, 2004

(51) Int. Cl.
*B01D 15/08* (2006.01)

(52) U.S. Cl. .................. 210/198.2; 210/101; 210/143; 210/656; 422/70

(58) Field of Classification Search ............ 210/635, 210/656, 101, 143; 422/70
See application file for complete search history.

(56) References Cited

FOREIGN PATENT DOCUMENTS

| JP | 56-97744 | 8/1981 |
|---|---|---|
| JP | 56-097744 | 8/1981 |
| JP | 63-282650 | 11/1988 |
| JP | 5-60736 | 3/1993 |
| JP | 6-201667 | 7/1994 |
| JP | 63-282650 | 11/1998 |
| JP | 11-248695 | 9/1999 |
| JP | 11-266864 | 10/1999 |

OTHER PUBLICATIONS

PTO 05-5733, Translation of Japanese Patent No. 6-201667, Aug. 2005, pp. 1-9.*
PTO 05-5716, Translation of Japanese Patent No. 11-248695, Aug. 2005, pp. 1-18.*

* cited by examiner

*Primary Examiner*—Ernest G. Therkorn
(74) *Attorney, Agent, or Firm*—Dickstein Shapiro Morin & Oshinsky LLP

(57) ABSTRACT

A solution such as a washing liquid can be passed through a separation column such as a nozzle tip having a solid phase quickly and reliably, thereby achieving improvements in throughput. A sample processing device comprises a separation column having a carrier capable of capturing a target substance, a liquid supply passage capable of supplying a liquid from one end portion of the separation column to the other end portion thereof, and a communication passage disposed independently of the liquid supply passage and capable of providing communication between the inside of the separation column and the outside. The communication between the inside of the separation column and the outside by the communication passage is controlled.

16 Claims, 9 Drawing Sheets

SAMPLE PROCESSING DEVICE AND SAMPLE PROCESSING METHOD

TECHNICAL FIELD

The present invention relates to a sample processing device and method for performing a process, such as washing, on a target substance such as a nucleic acid, using a solution such as a washing liquid.

BACKGROUND ART

With the progress of molecular biology, many genetic techniques have been developed, and many disease genes have been isolated and identified by these techniques. As a result, molecular biological techniques have also been incorporated in the field of medicine for the purpose of diagnosis or examination, so that it is now possible to perform types of diagnosis that had previously been extremely difficult, and the number of days necessary for examinations is being greatly reduced.

Such progress owes a lot to the practical application of the polymerase chain reaction (PCR) process in particular. The PCR process is capable of amplifying a nucleic acid in a solution in a sequence-specific manner. For example, it can indirectly prove the presence of a virus that exists only in an extremely minute amount in blood serum by amplifying and detecting a nucleic acid derived from that virus. The PCR process, however, has several problems when used for routine examinations in a clinical setting. Particularly, in preliminary processing where a nucleic acid is extracted from a biological sample, it is important to extract a highly purified nucleic acid in the purification step in order to maintain accuracy throughout the subsequent PCR process. Specifically, when extracting a nucleic acid from a biological sample in preliminary processing, the purification step must be carried out such that the nucleic acid can be separated in a pure form, with impurities eliminated to as great an extent as possible. For the purification of nucleic acids, several techniques have been proposed, as will be described below.

JP Patent Publication (Kokai) No. 11-266864 A (1999) discloses a method of automating the extraction of nucleic acids using a nucleic acid capturing tip in which a silica-containing solid phase is placed. In this technique, a nozzle tip is mounted on a movable liquid suction/discharge nozzle, and a binding accelerating agent for accelerating the binding of nucleic acid to the solid phase is sucked from a bottle. Then a nucleic acid-containing sample is sucked from a specimen container and a mixture solution of the binding accelerating agent and the sample is discharged into a reaction container. The nozzle tip is then discarded, and a nucleic acid capturing tip is newly mounted on the liquid suction/discharge movable nozzle. The mixture solution is sucked from the reaction container into the nucleic acid capturing tip. Then, the nucleic acid in the mixture solution that has been sucked from the reaction container is bound to the solid phase in the nucleic acid capturing tip, followed by discharge of the liquid in the nucleic acid capturing tip. Thereafter, the washing liquid in the washing container is sucked into the nucleic acid capturing tip and then discharged, such that the solid phase to which the nucleic acid is bound and the inside of the nucleic acid capturing tip are washed. Lastly, an eluent is sucked into the nucleic acid capturing tip, and then the eluent containing the nucleic acid separated from the solid phase is discharged into a purified product container. In this manner, a nucleic acid can be purified from a nucleic acid-containing sample.

Thus in the method disclosed in JP Patent Publication (Kokai) No. 11-266864 (1999), the solid phase to which nucleic acid is bound and the inside of the nucleic acid capturing tip are washed by sucking washing liquid from the washing container into the tip and then discharging it therefrom in a repeated manner. It takes more time for suction than for discharge due to the resistance of the solid phase, so that the method has a very poor washing efficiency and a significantly lowered throughput. Furthermore, should the washing liquid remain on the solid phase or the inside walls of the nucleic acid capturing tip, this would affect the concentration of the eluent and could possibly lower the nucleic acid purification performance.

Further, in the case of washing with a plurality of kinds of washing reagents, they are dispensed via the same flow path. As a result, interference is caused between one washing reagent and another upon switchover, which causes a reduction in concentration or dispensing accuracy, thereby possibly resulting in a lowered washing efficiency.

It is therefore the object of the invention to provide a sample processing device and method whereby a solution, such as a washing liquid, can be put through a separation column, such as a nozzle tip having a solid phase, quickly and reliably, so that an improved throughput can be achieved.

SUMMARY OF THE INVENTION

The present invention with which the aforementioned object has been achieved includes the following.

(1) A sample processing device comprising:
  a separation column with a carrier capable of capturing a target substance;
  a liquid supply passage capable of supplying a liquid from one end portion of said separation column to the other end portion thereof; and
  a communication passage disposed independently of said liquid supply passage and capable of allowing communication between the inside of said separation column and the outside,
  wherein:
  the communication provided between the inside and outside of said separation column by said communication passage is controlled.

(2) The sample processing device according to (1), wherein a plurality of said liquid supply passages are provided, wherein a different liquid is passed through each of said liquid supply passages.

(3) The sample processing device according to (2), wherein said plurality of liquid supply passages face said separation column at different heights.

(4) The sample processing device according to (1), wherein said communication passage is made of a tubular member enclosing said liquid supply passages, wherein a gas is passed through a gap formed between said liquid supply passages and the inner wall of said tubular member.

(5) The sample processing device according to (4), wherein a tip portion of said communication passage faces said separation column at a position higher than a tip portion of said liquid supply passages.

(6) The sample processing device according to (1), further comprising a gas supply passage disposed independently of said liquid supply passages and said communication passage, said gas supply passage being capable of supplying a gas from one end portion of said separation column to the other end portion thereof.

(7) The sample processing device according to (6), wherein a tip portion of said gas supply passage faces said separation column at a position higher than a tip portion of said liquid supply passage.

(8) The sample processing device according to (1), wherein a gas supply means is disposed in said communication passage that is capable of supplying a gas to the inside of said separation column.

(9) The sample processing device according to (6), wherein said gas supply passage is disposed inside said tubular member together with said liquid supply passage.

(10) A sample processing device comprising:
a separation column with a carrier capable of capturing a target substance;
a liquid supply passage capable of supplying a liquid from one end portion of said separation column to the other end portion thereof;
liquid supply means disposed at a starting portion of said liquid supply passage in order to supply a liquid to said separation column via said liquid supply passage;
a communication passage disposed independently of said liquid supply passage and capable of allowing communication between the inside of said separation column and the outside;
communication control means disposed at an intermediate portion of said communication passage for allowing and/or preventing communication between the inside of said separation column and the outside; and
control means for controlling at least the operation of said liquid supply means and that of said communication control means,
wherein:
said control means is capable of opening said communication passage by controlling said communication control means when supplying a liquid from said liquid supply means to said separation column via said liquid supply passage.

(11) The sample processing device according to (10), wherein a plurality of said liquid supply passages are provided and a plurality of liquid supply means are provided at individual starting portions of said liquid supply passages, wherein a different liquid is passed through each of said liquid supply passages.

(12) The sample processing device according to (11), wherein said plurality of liquid supply passages face said separation column at different heights.

(13) The sample processing device according to (10), wherein said communication passage is made of a tubular member enclosing said liquid supply passage, wherein a gas is passed through a gap formed between said liquid supply passage and the inner wall of said tubular member.

(14) The sample processing device according to (10), wherein a tip portion of said communication passage faces said separation column at a position higher than a tip portion of said liquid supply passage.

(15) The sample processing device according to (10), further comprising a gas supply passage disposed independently of said liquid supply passage and said communication passage, said gas supply passage being capable of supplying a gas from one end portion of said separation column to the other end portion thereof.

(16) The sample processing device according to (15), wherein a tip portion of said gas supply passage faces said separation column at a position higher than a tip portion of said liquid supply passage.

(17) The sample processing device according to (15), wherein said gas supply passage is disposed inside said tubular member together with said liquid supply passage.

(18) A sample processing method wherein, when a liquid is supplied to a separation column having a carrier capable of capturing a target substance, via one end portion of said separation column, the pressure in a spatial portion on the liquid-supplied side is made equal to the external air pressure.

(19) The sample processing method according to (18), wherein after the liquid is supplied to the separation column, the supplied liquid is discharged from one end portion of the separation column towards the other end portion thereof.

(20) The sample processing method according to (18), wherein a plurality of kinds of liquids are supplied using different liquid supply passages.

(21) The sample processing method according to (18), wherein a plurality of liquids are supplied using a plurality of liquid supply passages with tip portions positioned at different heights, such that the liquids are supplied via the liquid supply passages in an order corresponding to the increasing heights of the tip portions thereof.

(22) The sample processing method according to (18), wherein the liquid is supplied from one end portion of said separation column using a liquid supply passage, and then a tip portion of said liquid supply passage is injected with airblow.

(23) The sample processing method according to (22), wherein airblow is injected at a position higher than the tip portion of said liquid supply passage.

(24) The sample processing method according to (18), wherein said liquid is a washing liquid with which the inside of the separation column and a carrier contained in the separation column are washed.

(25) A sample processing method comprising:
a first step of applying a sample to a separation column having a carrier capable of capturing a target substance so that the target substance is captured on the carrier;
a second step of supplying a liquid to the inside of the separation column, with the pressure in a spatial portion at one end portion of the separation column being equalized to the external pressure; and
a third step of discharging the liquid supplied to the inside of the separation column from one end portion of the separation column to the other end portion thereof, with the spatial portion at one end portion of the separation column being closed.

(26) The sample processing method according to (25), wherein the second and third steps are repeated a number of times corresponding to the number of a plurality of kinds of liquids involved.

(27) The sample processing method according to (25), wherein, when repeating the second and third steps for a number of times corresponding to the number of a plurality of kinds of liquids involved, a plurality of liquid supply passages with tip portions positioned at different heights are used in an order corresponding to the increasing heights of the tip portions of the liquid supply passages.

(28) The sample processing method according to (25), wherein in the second step, the liquid is supplied from one end portion of the separation column using a liquid supply passage, and then a tip portion of said liquid supply passage is injected with airblow.

(29) The sample processing method according to (28), wherein airblow is injected at a position higher than the tip portion of said liquid supply passage.

(30) The sample processing method according to (25), wherein said liquid is a washing liquid with which the inside of the separation column and a carrier contained in the separation column are washed.

(31) A nucleic acid purifying apparatus comprising:
an input/output device;
a mechanism control portion adapted to receive instructions from said input/output device and to provide control results to the input/output device;
a plurality of liquid supply devices controlled by said control mechanism portion to supply a controlled amount of liquid;
a motor for driving said liquid supply devices;
a transport device for transporting said liquid supply devices in a desired direction;
a motor for controlling said transport device;
an electromagnetic valve controlled by said mechanism control portion to switch between an air filter and an air discharge pump; and
an electromagnetic valve controlled by said control portion to switch air passages.

BEST MODE OF CARRYING OUT THE INVENTION

Hereafter the sample processing device and method according to the invention will be described in more detail. In the following description, a nucleic acid purification apparatus will be described by way of example in which nucleic acid as a target substance is captured using a nucleic acid capturing tip as a separation column. The inside of the nucleic acid capturing tip is washed with a washing liquid, following which nucleic acid is extracted from the nucleic acid capturing tip. Such an embodiment, however, is merely illustrative and does not limit the technical scope of the present invention.

Figure 1:
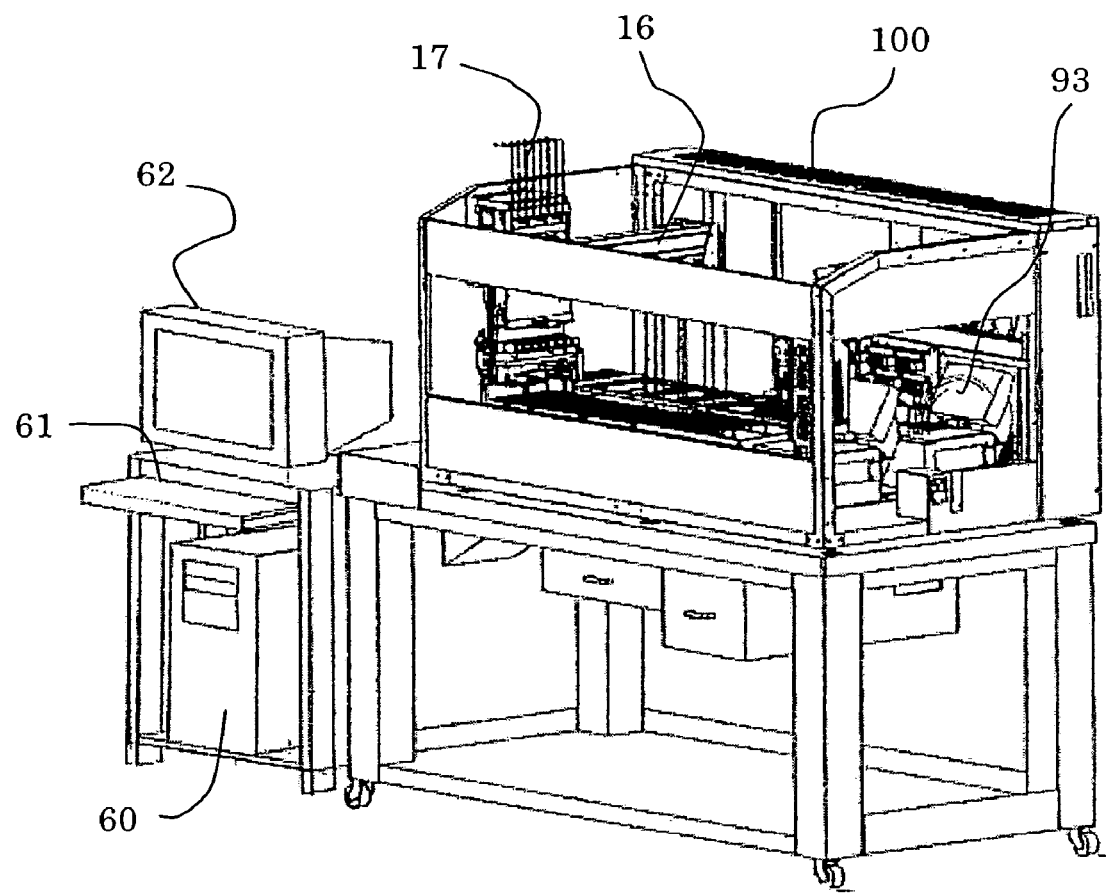
FIG. 1 is a perspective view of a nucleic acid purifying apparatus as an example of the present invention.

As shown in FIG. 1, a nucleic acid purifying apparatus 100 is connected to a personal computer (PC) 60. The personal computer 60 stores inputted operating conditions, specimen information and so on, and controls each step of the nucleic acid purification process. The personal computer 60 is connected to a keyboard 61 for entering operating conditions, specimen information and so on, and to a CRT 62 for displaying various kinds of information such as input information or warning information for the operator.

Figure 2:
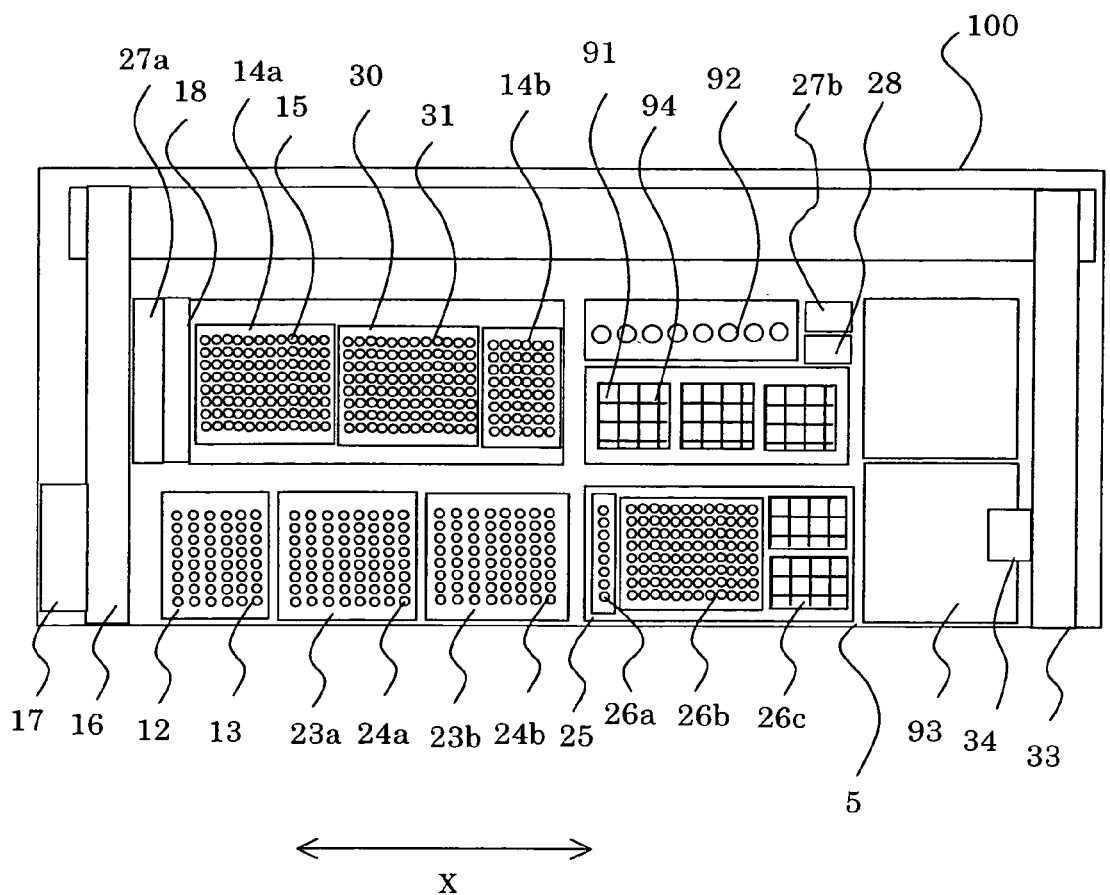
FIG. 2 is a plan view of a main portion of an operating table in the nucleic acid purifying apparatus.

As shown in FIG. 2, the nucleic acid purifying apparatus 100 includes two arms 16 and 33 that can be moved in a direction indicated by arrow X, and an operating plane 5 on which a thermal cycler 93 is provided, for example.

Figure 3:
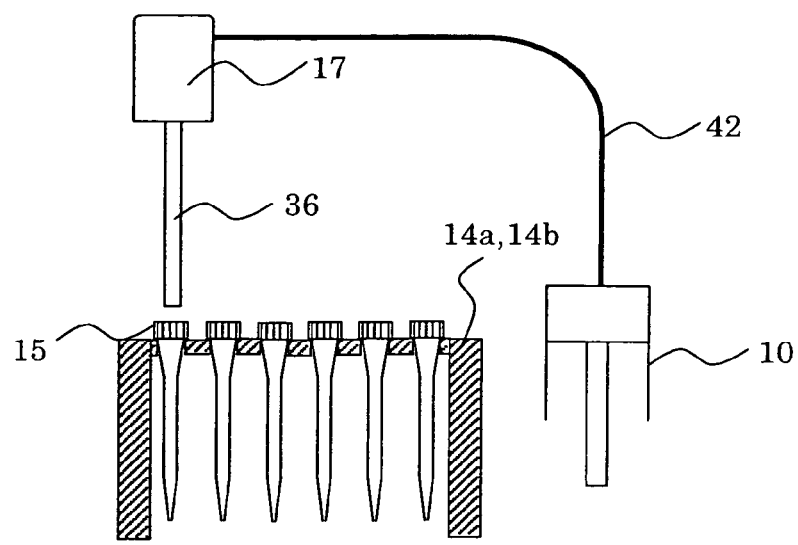
FIG. 3 schematically shows how a dispensing tip is mounted on a dispensing nozzle.

On the arm 16 is mounted a nozzle holder 17 holding a dispensing nozzle 36, as shown in FIG. 3. The nozzle holder 17 is movable in a direction perpendicular to the arrow X of FIG. 2, namely along the length of the arm 16. The nozzle holder 17 further possesses a drive control means by which the dispensing nozzle 36 can be driven towards or away from the operating table 5 as desired.

Figure 4:
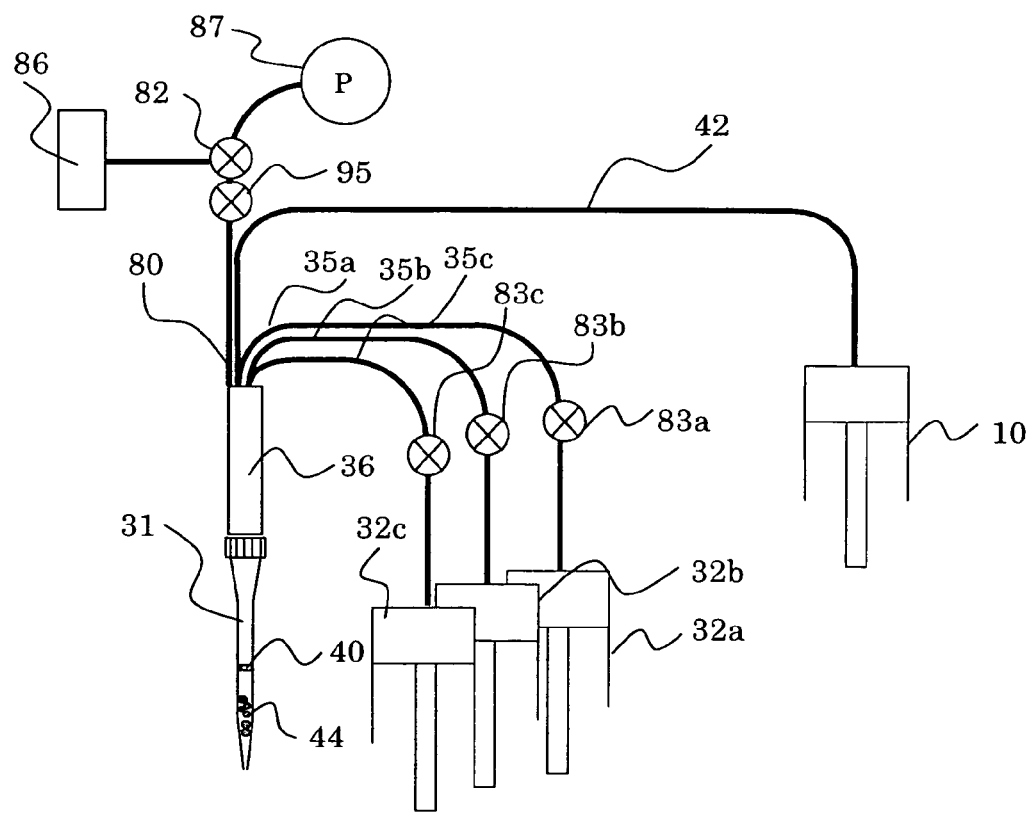
FIG. 4 schematically shows the arrangement of a washing liquid passage, an air passage and suction/discharge passages in the dispensing nozzle.

The dispensing nozzle 36 contains a washing liquid passage, air passage and suction/discharge passage independent from each other, as shown in FIG. 4.

The washing liquid passage is a liquid supply passage for supplying a washing liquid to the separation column mounted on the dispensing nozzle 36. The passage allows a washing liquid to be supplied to the separation column, such as a nucleic acid capturing tip, which will be described later. The washing liquid passage comprises three flexible pipes 35a, 35b and 35c, syringe pumps 32a, 32b and 32c for the supply of washing liquid, each connected to one end of the three pipes 35a, 35b and 35c, respectively, and electromagnetic valves 83a, 83b and 83c provided at an intermediate portion of the three pipes, respectively, for opening and closing the pipes. The inside of each syringe of the syringe pumps 32a, 32b and 32c for supplying washing liquid is connected to a washing liquid supply source in which a different washing liquid is stored, though not shown.

The air passage is a communicating passage for providing communication between the inside of the separation column mounted on the dispensing nozzle 36 and the outside of the column. For example, the pressure inside the nucleic acid capturing tip, the details of which will be described later, can be equalized with that of the outside by means of the air passage. The air passage comprises a flexible pipe 80, an air filter 86 and air discharge pump 87 provided at one end of the pipe 80, an electromagnetic valve 82 for switching between the air discharge pump 87 and the outside for connection with the pipe 80, and a pressure adjusting valve 95 provided at an intermediate portion of the pipe 80. The electromagnetic valve 82 is adapted to automatically close the pipe 80 when a predetermined pressure is exceeded, thus controlling the pressure. The air filter 86 is provided in a stage preceding that of the electromagnetic valve 82 in order to prevent the entry of foreign matter from the atmosphere into the pipe 80.

The suction/discharge passage is a gas supply passage and is provided independently of the washing liquid passage and the air passage. The suction/discharge passage is capable of supplying gas to the separation column, such as a nucleic acid capturing tip which will be described later, mounted on the dispensing nozzle 36. The suction/discharge passage comprises of a flexible pipe 42 and a syringe pump 10 connected to one end of the pipe 42. The inside of the syringe of the syringe pump 10 is connected to a pure water supply source (not shown) that contains pure water.

Figure 5:
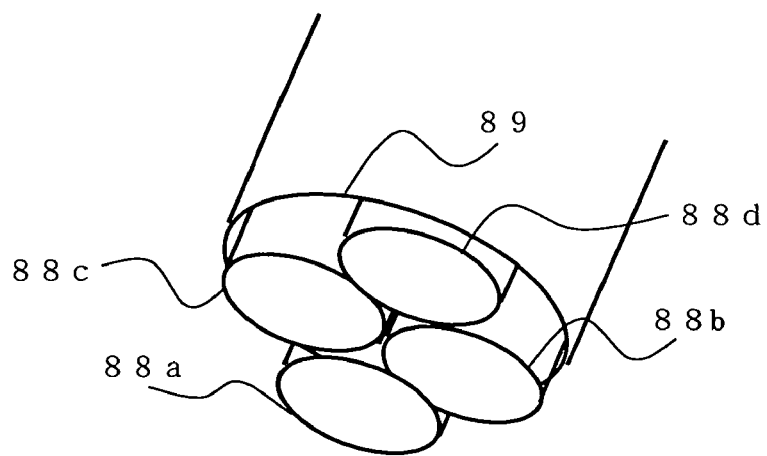
FIG. 5 is a perspective view of a main portion showing in enlargement the tip portions of the washing liquid passage, air passage and suction/discharge passages facing the inside of the dispensing nozzle.

Within the dispensing nozzle 36, the pipes 35a, 35b and 35c and the pipe 42 are accommodated in the pipe 80. Thus, the air supplied from the air discharge pump 87 passes through gaps between the outer walls of the pipes 35a, 35b and 35c and pipe 42 and the inner wall of the pipe 80 before being discharged via the tip of the dispensing nozzle 36. At the tip of the dispensing nozzle 36, the washing liquid passage and suction/discharge passage protrude beyond the air passage, as shown in FIG. 5. Specifically, a tip portion 88a of pipe 35a, a tip portion 88b of pipe 35b, a tip portion 88c of pipe 35c and a tip portion 88d of pipe 42 extend beyond a tip portion 89 of pipe 80.

On the arm 33 is mounted a nozzle holder 34 for holding a reagent discharge nozzle and a dispensing nozzle, for example. The nozzle holder 34 is mounted such that it can be moved in a direction perpendicular to the arrow X in FIG. 2, namely along the length of the arm 33. The nozzle holder 34 is provided with a drive control means for driving the reagent discharge nozzle towards and away from the operating table 5. The reagent discharge nozzle and the dispensing nozzle are connected to syringe pumps via individual pipes, though not shown, so that they can suck or discharge a desired solution.

In the nucleic acid purifying apparatus 100, as shown in FIG. 2, the operating plane 5 comprises a specimen rack 12 for holding a plurality of specimen containers 13, container racks 23a and 23b for holding a plurality of processing containers 24a and 24b, a container storage rack 25 for holding a plurality of purified product containers 26a, 26b and 26c, tip racks 14a and 14b for holding a plurality of dispensing tips 15, a tip rack 30 for holding a plurality of nucleic acid capturing tips 31, a tip rack 91 for holding a plurality of reagent dispensing tips 94, a plurality of reagent bottles 92, tip detachers 27a and 27b capable of detaching the dispensing tips 15, nucleic acid capturing tips 31 and reagent dispensing tips 94, a liquid reservoir portion 28 for the disposal of unwanted solution or the like, and a washing portion 18 for washing the dispensing tips 15 and the nucleic acid capturing tips 31.

The specimen rack 12 can hold a total of 48 specimen containers 13 arranged in eight rows and six columns, for example. The specimen containers 13 accommodate nucleic acid-containing samples, which include living-body samples such as whole blood, blood serum, sputum or urine, biological samples such as cultured cells or cultured bacteria, and substances such as a nucleic acid carried in a gel after electrophoresis, a reaction product of a DNA amplifying enzyme or the like, or a nucleic acid in a coarsely purified condition. The term nucleic acid herein includes double- or single-stranded, or partly double- or single-stranded deoxyribonucleic acids (DNA) and ribonucleic acids (RNA).

The container racks 23a and 23b have a temperature adjusting function for adjusting the temperatures of the processing containers 24a and 24b that are being held to desired temperatures. Thus, the temperatures of the processing containers 24a and 24b held in the container racks 23a and 23b and those of the solutions contained in the containers 24a and 24b can be maintained at desired temperatures by means of the temperature adjusting function.

The container storage rack 25 can hold containers 26a for large-sized purified products arranged in eight rows and a single column. It can also hold containers 26b for intermediate-sized purified products arranged in eight rows and 12 columns, and two 96-well purified product containers 26c, for example. The purified product containers 26a, 26b, and 26c accommodate purified solutions obtained by purifying a nucleic acid component from nucleic acid-containing samples.

The tip racks 14a and 14b comprise a plurality of openings for holding a plurality of dispensing tips 15, as shown in FIG. 3. The tip racks are formed in the shape of a box and have a height such that the tip portions of the dispensing tips 15 do not come into contact with the operating plane 5. Specifically, the plurality of dispensing tips 15 are held while being inserted into the openings in the tip racks 14a and 14b. The nozzle holder 17 comprises a dispensing nozzle 36 for mounting the dispensing tips 15, syringe pump 10 for controlling the pressure inside the dispensing nozzle 36, and flexible pipe 42 connecting the dispensing nozzle 36 and the syringe pump 10. During mounting, the dispensing tip 15 is press-fitted over the tip portion of the dispensing nozzle 36.

Figure 6:
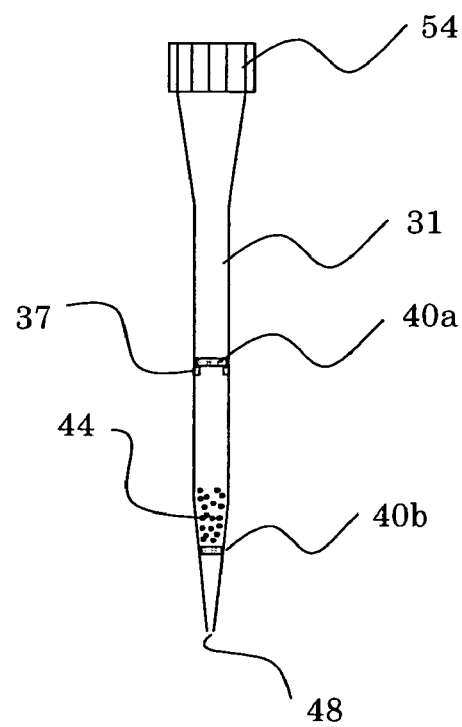
FIG. 6 is a side view of a nucleic acid capturing tip.

The tip rack 30 can hold the nucleic acid capturing tips 31 as shown in FIG. 6 in eight rows and 12 columns. The nucleic acid capturing tip 31 is formed such that its internal diameter gradually decreases from a head portion 54 towards a tip 48 at the bottom. The head portion 54 has an internal diameter such that the head can either fit with the tip portion of the dispensing nozzle 36 in an airtight manner or it can be press-fitted over the tip portion of the dispensing nozzle 36. The nucleic acid capturing tip 31 is formed of a transparent or semi-transparent synthetic resin, for example.

The nucleic acid capturing tip 31 is provided with disc-shaped blocking members 40a and 40b defining a space therebetween in which a solid phase 44 is accommodated. The blocking members 40a and 40b have many openings allowing the easy passage of a liquid or gas and yet the openings are of such a size that the leakage of the solid phase 44 is prevented. Thus, the solid phase 44 accommodated in the space between the blocking members 40a and 40b is prevented from leaking outside therefrom. The blocking members 40a and 40b are made of polyvinylidene fluoride, for example, which exhibits little non-specific adsorption of a nucleic acid component or the like and is hydrophilic. When a hydrophilic material such as polyvinylidene fluoride is used, the non-specific adsorption of protein or nucleic acid can be reduced so that the level of purification of nucleic acid or the yield can be increased.

The nucleic acid capturing tip 31 has a plurality of protruding insertion-facilitating guides 37 formed on the inner wall thereof. The insertion facilitating guides 37 function to regulate and position the blocking member 40a towards the head portion 54 in a vertical direction. The blocking member 40b towards the tip portion 48 is positioned as it is press-fitted.

The solid phase 44 may be, but is not limited to, a powder of flint glass (manufactured by Wako Pure Chemical Industries Ltd.), for example. With flint glass, which has a high silica content providing a nucleic acid-capturing effect, nucleic acid can be purified with a high yield. Other substances may be used as the solid phase 44 as long as they contain silicon oxide, such as glass particles, silica particles, quartz filter paper, quartz wool, crushed material thereof, or diatom earth, for example.

A reagent bottle 92 accommodates a reagent solution such as a binding accelerating agent. As a binding accelerating agent, preferably a substance should be selected that has little absorption at wavelengths of around 260 nm, where the absorption peak of nucleic acid exists. This is because of the fact that for assaying the purity or amount of a nucleic acid, absorption is in many cases measured at 260 nm using a spectroscope, and therefore a substance with an absorption peak at around 260 nm might affect the results of assay. Preferably, guanidine hydrochloride (GuHCl) should be used as the binding accelerating agent. The final concentration during use of guanidine hydrochloride should preferably be 4 to 6 mol/L.

Figure 7:
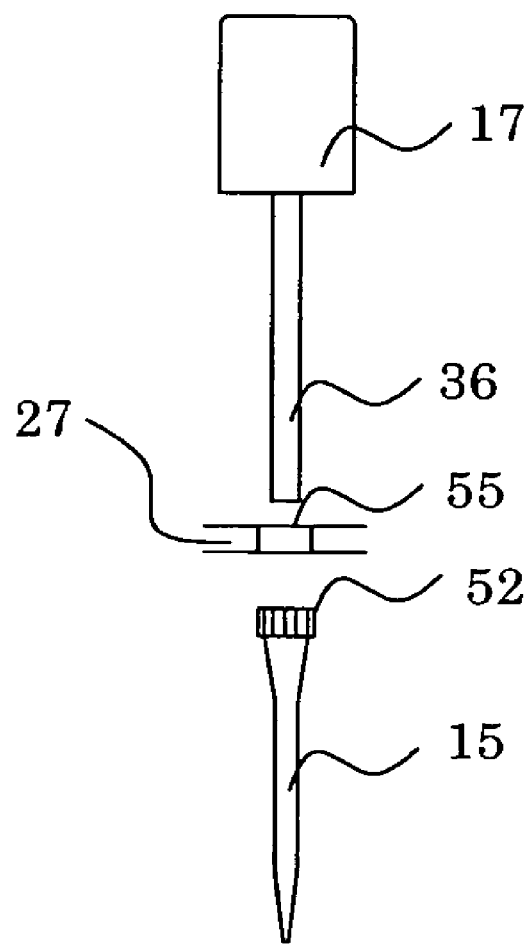
FIG. 7 schematically shows how the dispensing tip is detached from the dispensing nozzle using a tip detacher.

The tip detachers 27a and 27b are positioned at a predetermined height from the operating plane 5 and are made of a plate-like member with a slit 55, as shown in FIG. 7. The slit 55 is formed to have a width that is smaller than the external diameter of the head portion 52 of the dispensing tip 15 and the head portion 54 of the nucleic acid capturing tip 31 and larger than the external diameter of the dispensing nozzle 36. When detaching the dispensing tip 15, for example, from the dispensing nozzle 36 using the tip detacher 27a or 27b, first the arm 16 and nozzle holder 17 are driven to cause the dispensing nozzle 36 to enter the slit 55 while the head portion 52 is kept lower than the height at which the slit 55 is positioned. Then, the nozzle holder 17 is lifted such that the head portion 52 comes into contact with the lower surface of the plate-like member. The nozzle holder 17 is then further lifted until the tip 15 drops out of the dispensing nozzle 36.

The dispensing nozzle held by the nozzle holder 34 is connected to a syringe pump for supplying a dispenser reagent, though not shown. This syringe pump is connected to a bottle, for example, containing a dispenser reagent, such that the dispenser reagent can be sucked from the bottle and supplied to the dispensing nozzle. Examples of the dispenser reagent include a chaotropic agent such as guanidine thiocyanate.

Further, the reagent discharge nozzle held by the nozzle holder 34 is connected to a syringe pump for supplying an eluent, though not shown. This syringe pump is connected to a bottle containing an eluent such that the eluent can be sucked from the bottle and supplied to the reagent discharge nozzle.

The eluent may be, but is not limited to, an aqueous solution of low salt concentration (such as a Tris buffer solution (a mixed solution of 10 mmol/L of Trishydroxymethylaminomethane and 1 mmol/L of ethylene-diaminetetraacetic acid), for example) or water.

The nucleic acid purifying apparatus 100 comprises, at least, an input/output device, a mechanism control portion adapted to receive instructions from the input/output device and to feed control results to the input/output device, a plurality of liquid supply devices controlled by the control mechanism portion such that they supply a controlled liquid amount, a motor for driving the liquid supply devices, a transport device for moving the liquid supply devices in a desired direction, a motor for controlling the transport device, an electromagnetic valve adapted to switch between the air filter and the air discharging pump under the control of the mechanism control portion, and an electromagnetic valve for switching the air passages under the control of the control portion. Examples of the input/output device include a computer and a keyboard or a CRT connected to the computer. The liquid supply device may be a syringe pump, for example. The motor may be a stepping motor, for example. The transport device may be an arm, for example.

Figure 8:
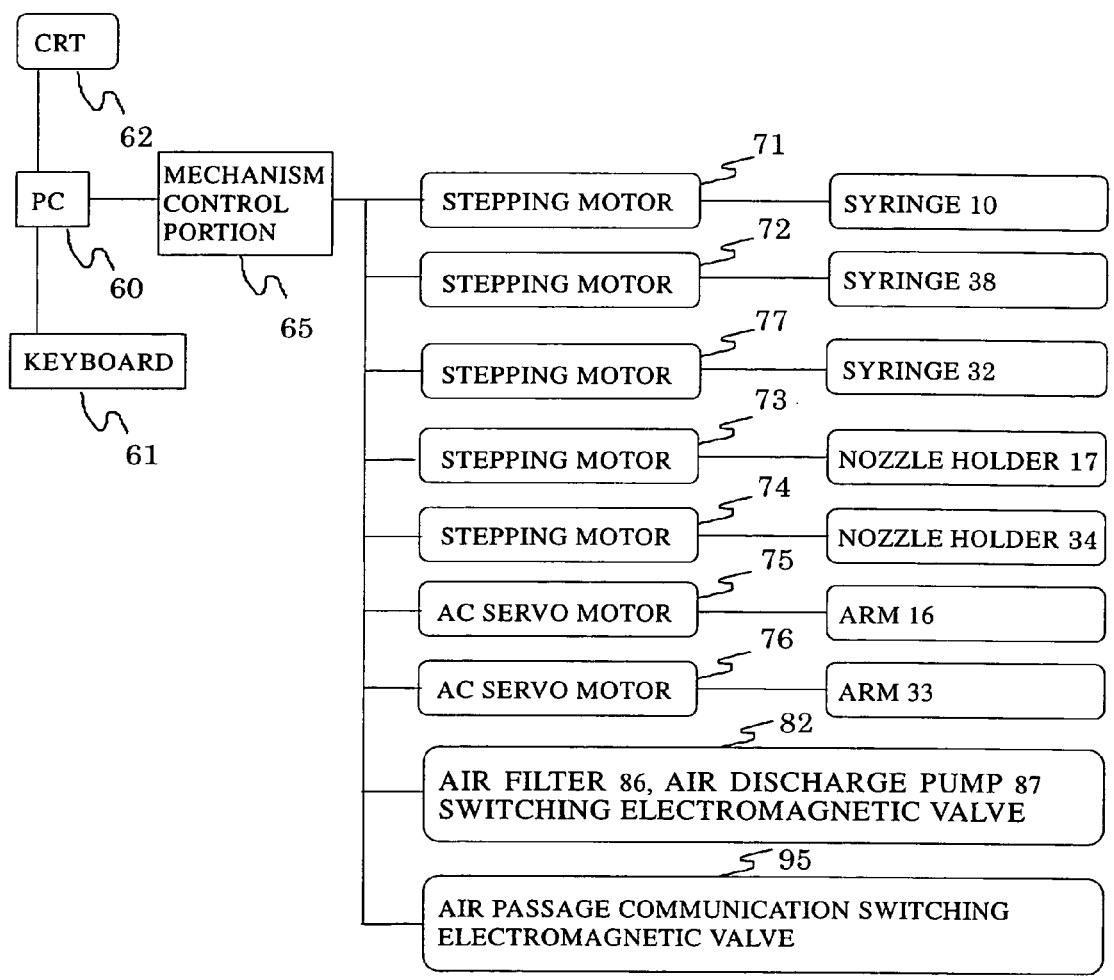
FIG. 8 is a block diagram of the electric system of the nucleic acid purifying apparatus.

Specifically, in the nucleic acid purifying apparatus 100, a keyboard 61, a CRT 62 and a mechanism control portion 65 are connected to a PC 60, as shown in FIG. 8. The mechanism control portion 65 controls, for example, a stepping motor 71 for driving a piston for causing the syringe pump 10 to carry out a suction/discharge operation, a stepping motor 72 for driving a piston for causing the syringe pump 38 for supplying a reagent to the reagent discharge nozzle to perform a suction/discharge operation, a stepping motor 77 for driving a piston for causing the syringe pumps 32a, 32b and 32c to carry out a suction/discharge operation, a stepping motor 73 for moving the nozzle holder 17 horizontally and vertically, a stepping motor 74 for moving the nozzle holder 34 horizontally and vertically, an AC servo motor 75 for moving the arm 16 horizontally, an AC servo motor 76 for moving the arm 33 horizontally, an electromagnetic valve 82 for switching between the air filter 86 and air discharge pump, and an electromagnetic valve 95 for adjusting communication through the air passage. In FIG. 8, the syringes 32a, 32b and 32c are indicated collectively as "SYRINGE 32."

Figure 9:
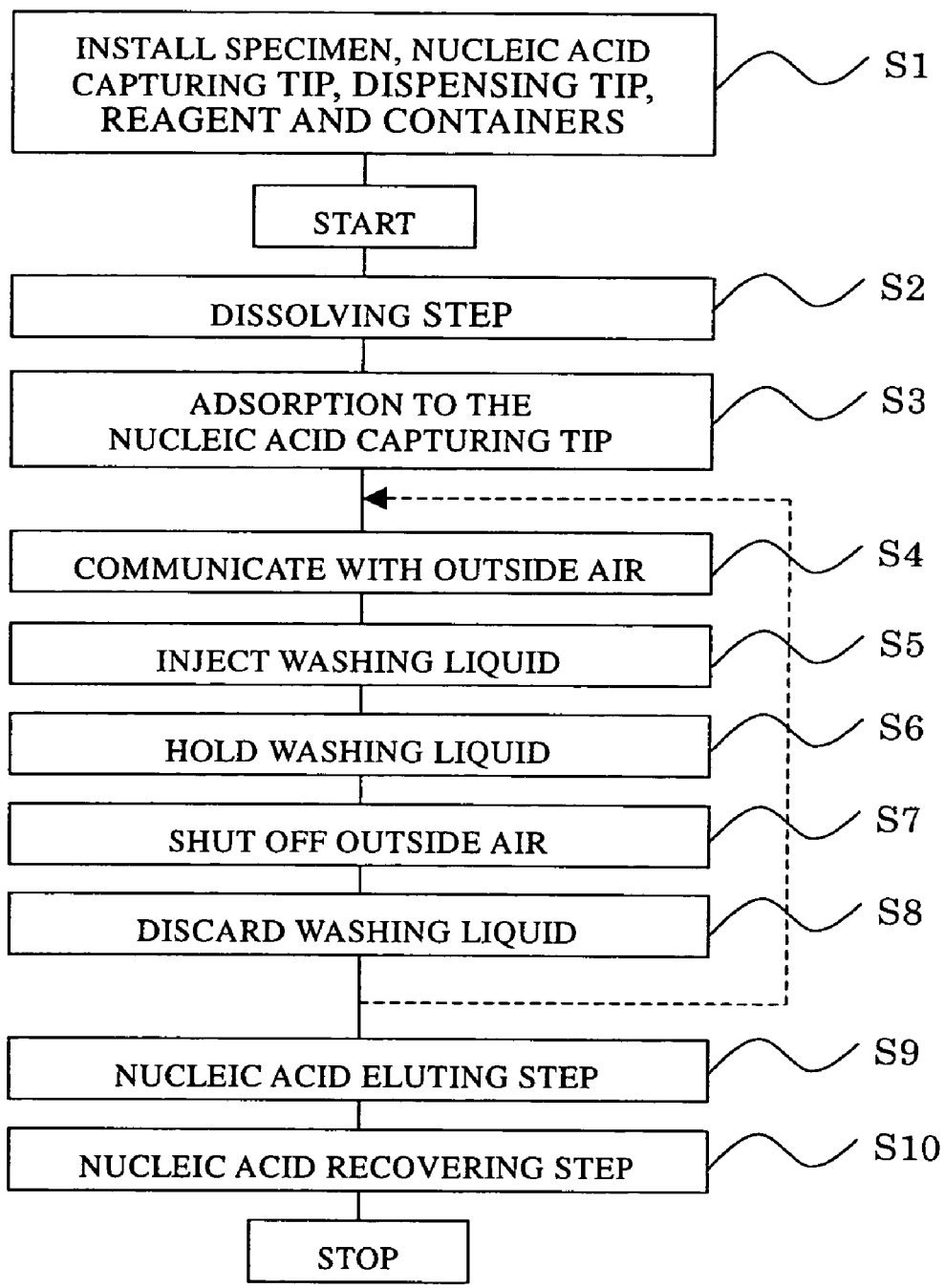
FIG. 9 is a flowchart of the process of purifying nucleic acid using the nucleic acid purifying apparatus.

The stepping motor 71, the electromagnetic valve 82 and so on shown in FIG. 8 are operated in accordance with a predetermined program stored in PC 60 under the control of the mechanism control portion 65. The program may be set as desired by the operator using the keyboard 61 or the like. The thus configured nucleic acid purifying apparatus 100 can therefore extract nucleic acid from a nucleic acid-containing sample and purify it as shown in the flowchart of FIG. 9, in accordance with the program.

In step 1 (indicated as S1 in FIG. 9; other steps are indicated in a like manner hereafter), prior to the operation for purifying from a nucleic acid-containing sample, a specimen from which nucleic acid is to be extracted is placed in the specimen container 13 and held in the specimen rack, and the specimen rack 12 is set at a predetermined position. Also in step 1, the tip rack 14a holding the dispensing tips 15, the tip rack 30 holding the nucleic acid capturing tips 31, the tip rack 91 holding the reagent dispensing tips 94, the reagent bottle 92, the processing containers 24a and 24b, and the purified product containers 26a, 26b and 26c are set at their predetermined positions.

When extracting nucleic acid from the nucleic acid-containing sample, first a dissolving process is conducted in step 2 (S2). In the dissolving process, the arm 33 and nozzle holder 34 are driven to transport the reagent discharge nozzle above the tip rack 91. Then, the nozzle holder 34 is lowered so that the reagent dispensing tip 94 can be fitted on the reagent discharge nozzle. The arm 33 and nozzle holder 34 are then driven to transport the reagent dispensing tip 94 above the reagent bottle 92 accommodating a binding accelerating agent. The nozzle holder 34 is then lowered to thereby lower the reagent dispensing tip 94 into the reagent bottle 92, while the syringe pump 38 is activated to suck a predetermined amount of binding accelerating agent into the reagent dispensing tip 94. After driving and transporting the arm 33 and nozzle holder 34 above the processing containers 24a, the binding accelerating agent sucked into the reagent dispensing tip 94 is discharged into a predetermined processing container 24a. Thereafter, the arm 33 and nozzle holder 34 are driven and moved to the tip detacher 27b, where the reagent dispensing tip 94 that has been used is detached.

Then, the arm 16 and nozzle holder 17 are driven to transport the dispensing nozzle 36 above the tip rack 14a. The nozzle holder 17 is then lowered to thereby fit a dispensing tip 15 on the dispensing nozzle 36. The arm 16 and nozzle holder 17 are then driven to move the dispensing nozzle 36 to a predetermined specimen container 13 held in the specimen rack 12. The dispensing tip 15 is then lowered into the specimen container 13, while a predetermined amount of nucleic acid-containing sample is sucked into the dispensing tip 15 by the sucking action of the syringe pump 10.

The arm 16 and nozzle holder 17 are then driven to transport the dispensing tip 15 into which the nucleic acid-containing sample has been sucked above the processing container 24a in which the binding accelerating agent is accommodated. The dispensing tip 15 is then lowered into the processing container 24a, while the entire volume of the nucleic acid-containing sample is discharged into the processing container 24a. Thereafter, the operation of sucking and then discharging the solution in the processing container 24a using the dispensing tip 15 is repeated at least once, thereby mixing the nucleic acid-containing sample and the binding accelerating agent. The arm 16 and nozzle holder 17 are then driven to transport the dispensing tip 15 above the tip detacher 27a at the standby position.

Then, the arm 33 and nozzle holder 34 are driven to transport the nozzle holder 34 to the processing container 24a accommodating the nucleic acid-containing sample and binding accelerating agent. The syringe pump connected to the dispensing nozzle is then activated to discharge a specified amount of dispenser reagent. The arm 33 and nozzle holder 34 are then driven and transported above the tip detacher 27b to the standby position.

The arm 16 and nozzle holder 17 are then driven to transport the dispensing tip 15 that has been on standby above the tip detacher 27a above the processing container 24a in which the nucleic acid-containing sample, binding accelerating agent and dispenser reagent are accommodated. Then, the process of sucking the entire solution in the processing container 24a into the dispensing tip 15 and then discharging it is repeated at least once. As a result, the nucleic acid-containing sample, binding accelerating agent and dispenser reagent can be mixed within the processing container 24a.

The arm 33 and nozzle holder 34 are then driven to transport the nozzle holder 34 above the processing container 24a accommodating the nucleic acid-containing sample and the like. Then, the syringe pump connected to the dispensing nozzle is activated to discharge a prescribed amount of a second dispenser reagent. The arm 33 and nozzle holder 34 are then driven to transport the nozzle holder 34 to the position of the tip detacher 27b at the standby position.

Then, the arm 16 and nozzle holder 17 are driven to transport the dispensing tip 15 that has been on standby above the processing container 24a in which the nucleic acid-containing sample is accommodated. The syringe pump 10 is then activated in order to repeat at least once the operation of sucking the entire solution in the processing container 24a into the dispensing tip 15 and then discharging it. As a result, the nucleic acid-containing sample, binding accelerating agent, dispenser reagent and the second dispenser reagent can be mixed in the processing container 24a. The arm 16 and nozzle holder 17 are then driven to transport the dispensing tip 15 to the tip detacher 27b, where the dispensing tip 15 that has been used is detached in accordance with the detaching operation described above. Then, the arm 16 and nozzle holder 17 are driven to transport the dispensing nozzle 36 above the washing portion 18. Then, the tip of the dispensing nozzle 36 is washed by discharging a predetermined amount of pure water via the tip portion 88d of the dispensing nozzle 36. Thereafter, a small amount of air is sucked into the tip portion 88d of the dispensing nozzle 36, thus putting the nozzle 36 on standby.

Next, in step 3 (S3), the nucleic acid component contained in the mixed solution in the processing container 24a is allowed to be adsorbed to the solid phase 44, using the nucleic acid capturing tip 31. First, the arm 16 and nozzle holder 17 are driven to transport the dispensing nozzle 36 above the tip rack 30. The nozzle holder 17 is then lowered so that the nucleic acid capturing tip 31 can be fitted on the dispensing nozzle 36. The arm 16 and nozzle holder 17 are then driven to transport the nucleic acid capturing tip 31 above the processing container 24a accommodating the nucleic acid-containing sample and the like. The nozzle holder 17 is then lowered so that the nucleic acid capturing tip 31 can be lowered into the processing container 24a, while the syringe pump 10 is activated to suck the entire volume of the solution including the nucleic acid-containing sample into the nucleic acid capturing tip 31. As a result, the solid phase 44 in the nucleic acid capturing tip 31 comes into contact with the solution. Then, the syringe pump 10 is activated to repeat the process of discharging the solution sucked into the nucleic acid capturing tip 31 back into the processing container 24a and then sucking the discharged solution into the nucleic acid capturing tip 31 a plurality of times. In this way, the frequency of the surface of the solid phase 44 coming into contact with the solution can be increased, such that the efficiency of adsorption of nucleic acid by the solid phase 44 can be improved.

Then, the syringe pump 10 is activated to suck the entire volume of the solution in the processing container 24a into the nucleic acid capturing tip 31. In this state, the arm 16 and nozzle holder 17 are driven to transport the dispensing nozzle 36 above the washing portion 18, while the syringe pump 10 is activated to discharge the solution inside the nucleic acid capturing tip 31 into the washing portion 18.

Figure 10:
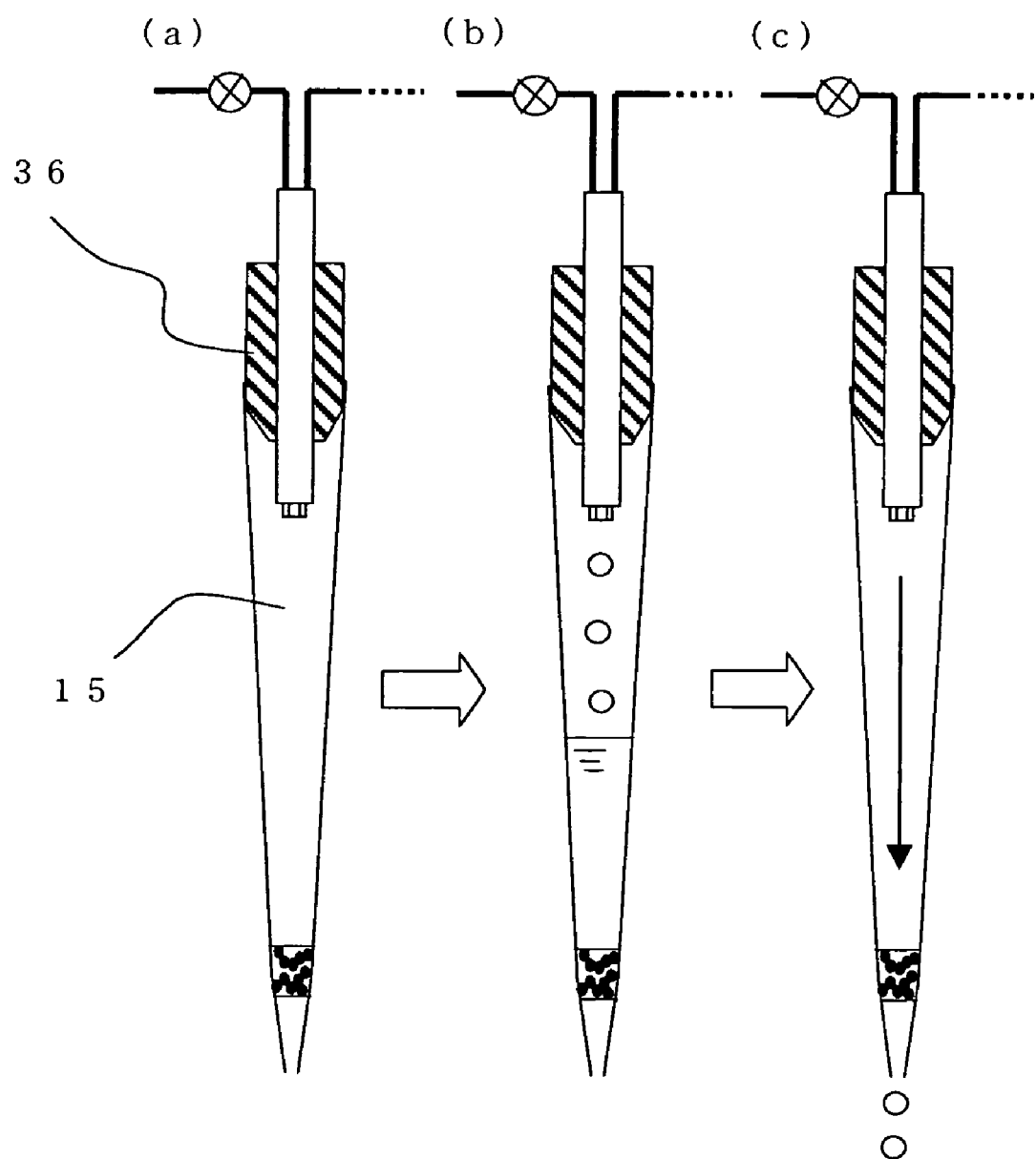
FIG. 10 shows side views of a main portion of the nucleic acid capturing tip in chronological order (from (a) to (c)) as the inside of the tip is washed.

Next, in the nucleic acid purifying apparatus, the washing process indicated in steps 4 (S4) to 8 (S8) is repeated a number of times corresponding to the types of the washing liquid. The washing process is a process for removing impurities (components other than nucleic acid) attached to the inner walls of the nucleic acid capturing tip 31 or the solid phase 44. In step 4 (S4), a passage opening and closing electromagnetic valve 83a is activated to connect the syringe pump 32a and the nucleic acid capturing tip 31, while the air switching valve 82 is activated to physically connect the inside and outside of the nucleic acid capturing tip 31 (as shown in FIG. 10(a)). As a result, the pressure inside the nucleic acid capturing tip 31 is constantly made equal to the external pressure.

Then, in step 5 (S5), the syringe pump 32a is activated to inject the washing liquid into the nucleic acid capturing tip 31 via the passage 35a. The washing liquid may be injected using any means other than the syringe pump 32a as long as the means is capable of transferring liquid, examples including a bellows pump or a Perista pump. The pressure inside the nucleic acid capturing tip 31 is constantly equal to the external pressure and does not increase even when the washing liquid is injected, so that the washing liquid is not discharged from the tip of the nucleic acid capturing tip 31 but instead remains inside the nucleic acid capturing tip 31 temporarily, as shown in FIG. 10(b). Thus, in step 6 (S6), the washing liquid is held inside the nucleic acid capturing tip 31.

Thereafter, in step 7 (S7), the air switching valve 82 is activated to separate the inside of the nucleic acid capturing tip 31 from the outside. Next in step 8 (S8), the air discharge pump 87 is activated to supply air into the nucleic acid capturing tip 31 via the air passage. Thus, the washing liquid injected into the nucleic acid capturing tip 31 can be caused to flow in one direction from the head portion 54 towards the tip portion 48, as shown in FIG. 10(c). The washing liquid passes through the nucleic acid capturing tip 31 and is continuously discharged as is via the tip portion 48 into the washing portion 18. By such a washing operation, impurities (components other than nucleic acid) attached to the inner walls of the nucleic acid capturing tip 31 and the surface of the solid phase 44 can be removed.

In case the washing liquid to be discharged is highly viscous and cannot be discharged with the air discharge pump 87 alone, the air switching valve 82 is first activated in step 8 to connect the outside and the syringe pump 10 via the nucleic acid capturing tip 31. In this state, the syringe pump 10 is activated to suck air into the syringe pump 10. Then, the air switching valve 82 is activated to separate the syringe pump 10 from the outside, and thereafter the syringe pump 10 is activated. In this way, air can be supplied into the nucleic acid capturing tip 31 via the gas supply passage to thereby push out the washing liquid that is being held. By repeating this operation, even a highly viscous washing liquid can be reliably discharged.

Then, impurities (components other than nucleic acid) attached to the inner walls of the nucleic acid capturing tip 31 or the solid phase 44 are reliably removed using a second and a third washing liquid in sequence in the same manner as described above. During the washing using the second washing liquid, the syringe pump 32*b*, passage opening and closing electromagnetic valve 83*b* and passage 35*b* are used in steps 4 to 8. During the washing using the third washing liquid, the syringe pump 32*c*, passage opening and closing electromagnetic valve 83*c* and passage 35*c* are used in steps 4 to 8. After the washing operations using the washing liquid, the second washing liquid and the third washing liquid is finished, the arm 16 and nozzle holder 17 are driven to transport the nucleic acid capturing tip 31 above the liquid reservoir portion 28, where the tip is put on standby.

During the washing for removing impurities (components other than nucleic acid) attached to the inner walls of the nucleic acid capturing tip 31 or to the solid phase 44, air is injected from the tip portion 88*d* towards the tip portions 88*a*, 88*b* and 88*c* as they discharge the various washing liquids. Thus, the washing liquid can be prevented from scattering around excessively and the washing efficiency of the nucleic acid capturing tip 31 can be improved.

The initial washing liquid can be discharged via the nozzle 88*a* using the syringe pump 32*a*, the second washing liquid can be discharged via the nozzle 88*b* using the syringe pump 32*b*, and the third washing liquid can be discharged via the nozzle 88*c* using the syringe pump 32*c*. In other words, the various washing liquids can be discharged via individual, independent passages. Thus, carryover between the various washing liquids can be prevented, as can reductions in concentration or dispensing accuracy.

Next, in step 9 (S9), a nucleic acid eluting process is conducted to elute the nucleic acid attached to the solid phase 44 in the nucleic acid capturing tip 31. Initially in the nucleic acid eluting process, the arm 33 and nozzle holder 34 are driven to transport the nozzle holder 34 above the container rack 23*b*. Then the syringe pump connected to a bottle containing an eluent is activated to discharge a single portion of eluent into the processing container 24*b*. The arm 33 and nozzle holder 34 are then driven to transport a reagent dispensing tip 94 above the tip detacher portion 27*b* where the tip is put on standby.

The arm 16 and nozzle holder 17 are then driven to transport the nucleic acid capturing tip 31 above the processing container 24*b* accommodating the eluent. Then, the syringe pump 10 is activated to suck the eluent in the processing container 24*b* into the nucleic acid capturing tip 31. As a result, the eluent comes into contact with the solid phase 44, so that the nucleic acid adsorbed to the surface of the solid phase 44 can be eluted in the eluent. After the eluent that has been sucked into the nucleic acid capturing tip 31 is discharged back into the processing container 24*b*, the operation of sucking and discharging the eluent using the nucleic acid capturing tip 31 is repeated a plurality of times, so that the nucleic acid attached to the solid phase 44 can be efficiently eluted.

The arm 33 and nozzle holder 34 are then driven to transport the nozzle holder 34 above another processing container 24*b* different from the processing container 24*b* used in the above-described process. Then, the next single portion of eluent is discharged into this other processing container 24*b* in the same manner as described above. The arm 16 and nozzle holder 17 are then driven to transport the nucleic acid capturing tip 31 above the other processing container 24*b*, and the nucleic acid attached to the solid phase 44 is reliably eluted in the eluent in the same manner as described above.

The arm 16 and nozzle holder 17 are then driven to transport the nucleic acid capturing tip 31 above the tip detacher 27*a*. Then, as shown in FIG. 7, the nucleic acid capturing tip 31 is detached from the dispensing nozzle 36 using the tip detacher 27*a*.

In step 10 (S10) next, a nucleic acid recovery process is conducted to recover the eluent discharged into the two processing containers 24*b*. In the nucleic acid recovery process, the arm 16 and nozzle holder 17 are initially driven to transport the dispensing nozzle 36 above the tip rack 14*b*. The nozzle holder 17 is then lowered so that the dispensing tip 15 can be fitted on the dispensing nozzle 36. Then, the arm 16 and nozzle holder 17 are driven to transport the dispensing nozzle 36 above the reaction container 24*b* in which the eluent obtained by the first eluting operation is accommodated. Then, the syringe pump 10 is activated to suck the entire volume of the eluent in the reaction container 24*b* into the dispensing tip 15.

The arm 16 and nozzle holder 17 are then driven to transport the dispensing nozzle 36 above a predetermined purified product container 26*a*. Then, the syringe pump 10 is activated to discharge the eluent sucked into the dispensing tip 15 into the purified product container 26*a*.

Then, the arm 16 and nozzle holder 17 are driven to transport the dispensing nozzle 36 above the reaction container 24*b* in which the eluent obtained by the second eluting operation is accommodated. The syringe pump is then activated to suck the entire volume of the eluent in the reaction container 24*b* into the dispensing tip 15. Then, the arm 16 and nozzle holder 17 are driven to transport the dispensing nozzle 36 above the purified product container 26*a* into which the eluent has previously been discharged. The syringe pump 10 is then activated to discharge the eluent sucked into the dispensing tip into the purified product container 26*a*.

Thus, in the purified product container 26*a*, the eluent containing the nucleic acid eluted from the solid phase 44 is recovered. Then, the arm 16 and nozzle holder 17 are driven to transport the dispensing and agitation nozzle 36 above the tip detacher 27*a*, with which the dispensing tip 15*a* is detached from the dispensing and agitation nozzle 36. The arm 16 and nozzle holder 17 are then driven to transport the dispensing nozzle 36 above the washing portion 18. After water is discharged from the tip of the dispensing nozzle 36, a minute quantity of air is sucked into the tip of the dispensing nozzle 36 so that the tip of the dispensing nozzle 36 can be washed.

This completes the operation for purifying nucleic acid from the nucleic acid-containing sample accommodated in the predetermined specimen container 13. The dispensing nozzle 36 remains above the washing portion 18 even after the washing of the tip is finished to prepare for the next purifying operation. A purifying operation for the next nucleic acid-containing sample can be conducted by performing the above-described processes.

When performing the purifying operation for the next nucleic acid-containing sample, processing containers 24a and 24b and purified product container 26 different from those used for the previous purifying operation will be used. Thus, nucleic acid can be recovered from each specimen container 13 in the plurality of purified product containers 26 held in the container storage rack 25 without the nucleic acid-containing samples contaminating each other.

While in the present example the dispensing nozzle 36 includes washing liquid passages comprising three pipes 35a, 35b and 35c, more washing liquid passages can be provided by increasing the number of pipes in the dispensing nozzle 36. Further, the pipes in the dispensing nozzle 36 may be used as passages for liquids other than the washing liquid or gases other than air.

Figure 11:
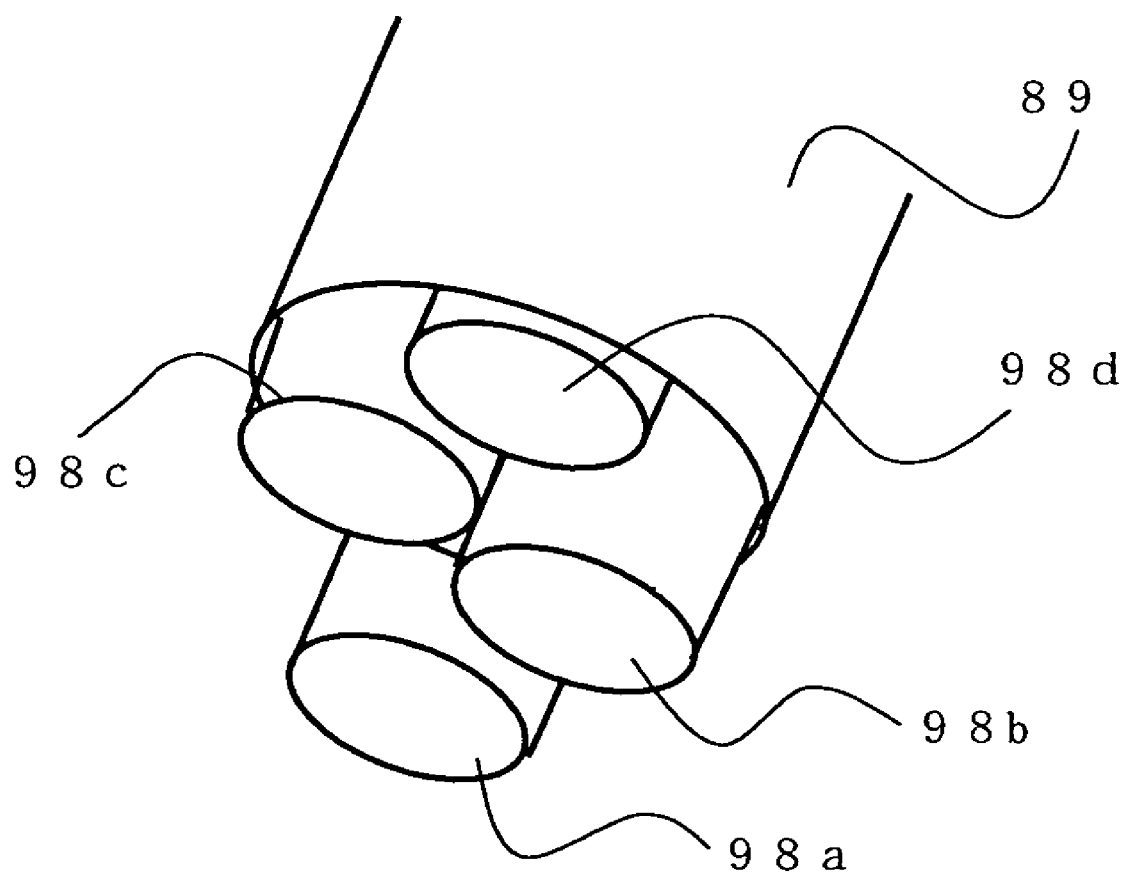
FIG. 11 is a perspective view of a main portion of another example of the tip portions of the washing liquid passage, air passage and suction/discharge passages facing the inside of the dispensing nozzle.

At the tip of the dispensing nozzle 36, the tip of the individual pipes forming the washing liquid passages may be cut at different heights as shown in FIG. 11, for example. In the illustrated case, the three pipes 35a, 35b and 35c are arranged such that the heights of the tip portions from highest to lowest are as follows: tip portion 98a of pipe 35a, tip portion 98b of pipe 35b, tip portion 98c of pipe 35c, and tip portion 98d of pipe 35d.

In the nucleic acid purifying apparatus equipped with the dispensing nozzle 36 as shown in FIG. 11, the pipes 35a, 35b and 35c discharge different kinds of washing liquid in that order. For example, a predetermined washing liquid is discharged from the pipe 35a and then another washing liquid is discharged via the tip portion 98b of the pipe 35b, such that the predetermined washing liquid remaining, if any, on the tip portion 98a can be removed. In this case particularly, there is no need to perform airblow for removing the remaining washing liquid on the tip portion 98a, so that the process can be simplified when involving a plurality of washing liquids and the washing can be performed more efficiently.

While in the above-described example the nucleic acid capturing tip 31 including the solid phase 44 for capturing nucleic acid has been described as an example of the separation column, the separation column in the present invention is not limited to the nucleic acid capturing tip 31. For example, the separation column may be a separation column used for liquid chromatography which comprises a mobile layer capable of capturing a target substance, or it may be a B/F separating portion of an immunoassay apparatus. In these cases, the target substance is an antigen, an antibody, hapten, or the like. The invention can be applied to any sample processing apparatus equipped with any of the aforementioned separation columns.

Specifically, in the present invention, the target substance is not limited to nucleic acid and may be a protein, an antibody, an antigen, or hapten, for example. Further, in the present invention, to "process" any of the aforementioned target substances means not only washing a target substance captured in the separation column but also causing a desired reaction in the target substance or extracting the target substance from the separation column. Thus, the present invention can be applied when carrying out processes in which a liquid is caused to act on a target substance captured in the separation column.

All publications, patents and patent applications cited herein are incorporated herein by reference in their entirety.

INDUSTRIAL FIELD OF APPLICATION

As described above in detail, in accordance with the sample purifying apparatus and method according to the invention, a liquid can be easily injected into a separation column and the thus injected liquid can be allowed to remain inside a separating tip. Thus, in accordance with the invention, a liquid can be passed through the separation column quickly and reliably, so that improvements in throughput can be achieved.

The invention claimed is:

1. A sample processing device comprising:
   a separation column with a carrier capable of capturing a target substance;
   a liquid supply passage capable of supplying a liquid from one end portion of said separation column to the other end portion thereof; and
   a communication passage disposed independently of said liquid supply passage and capable of communicating the inside of said separation column with the outside,
   and wherein a plurality of said liquid supply passages are provided, wherein a different liquid is passed through each of said liquid supply passages.

2. The sample processing device according to claim 1, wherein said plurality of liquid supply passages face said separation column at different heights.

3. The sample processing device according to claim 1, wherein said communication passage is made of a tubular member enclosing said liquid supply passages, wherein a gas is passed through a gap formed between said liquid supply passages and the inner wall of said tubular member.

4. The sample processing device according to claim 3, wherein a tip portion of said communication passage faces said separation column at a position higher than a tip portion of said liquid supply passages.

5. The sample processing device according to claim 1, further comprising a gas supply passage disposed independently of said liquid supply passages and said communication passage, said gas supply passage being capable of supplying a gas from one end portion of said separation column to the other end portion thereof.

6. The sample processing device according to claim 5, wherein a tip portion of said gas supply passage faces said separation column at a position higher than a tip portion of said liquid supply passage.

7. The sample processing device according to claim 1, wherein a gas supply means is disposed in said communication passage that is capable of supplying a gas to the inside of said separation column.

8. The sample processing device according to claim 5, wherein said gas supply passage is disposed inside said tubular member together with said liquid supply passage.

9. A sample processing device comprising:
   a separation column with a carrier capable of capturing a target substance;
   a liquid supply passage capable of supplying a liquid from one end portion of said separation column to the other end portion thereof;
   liquid supply means disposed at a starting portion of said liquid supply passage in order to supply a liquid to said separation column via said liquid supply passage;

a communication passage disposed independently of said liquid supply passage and capable of allowing communication between the inside of said separation column and the outside;

communication control means disposed at an intermediate portion of said communication passage for allowing and/or preventing communication between the inside of said separation column and the outside; and control means for controlling at least the operation of said liquid supply means and that of said communication control means, and wherein a plurality of said liquid supply passages are provided and a plurality of liquid supply means are provided at individual starting portions of said liquid supply passages, wherein a different liquid is passad though each of said liquid supply passages.

10. The sample processing device according to claim 9, wherein said plurality of liquid supply passages face said separation column at different heights.

11. The sample processing device according to claim 9, wherein said communication passage is made of a tubular member enclosing said liquid supply passage, wherein a gas is passed through a gap formed between said liquid supply passage and the inner wall of said tubular member.

12. The sample processing device according to claim 9, wherein a tip portion of said communication passage faces said separation column at a position higher than a tip portion of said liquid supply passage.

13. The sample processing device according to claim 9, further comprising a gas supply passage disposed independently of said liquid supply passage and said communication passage, said gas supply passage being capable of supplying a gas from one end portion of said separation column to the other end portion thereof.

14. The sample processing device according to claim 13, wherein a tip portion of said gas supply passage faces said separation column at a position higher than a tip portion of said liquid supply passage.

15. The sample processing device according to claim 13, wherein said gas supply passage is disposed inside said tubular member together with said liquid supply passage.

16. A nucleic acid purifying apparatus comprising:
an input/output device;
a mechanism control portion adapted to receive instructions from said input/output device and to provide control results to said input/output device;
a plurality of liquid supply devices controlled by said control mechanism portion to supply a controlled amount of liquid;
a motor for driving said liquid supply devices;
a transport device for transporting said liquid supply devices in a desired direction;
a motor for controlling said transport device;
air passages communicating with separation columns;
an electromagnetic valve controlled by said mechanism control portion to switch between an air filter and an air discharge pump; and
an electromagnetic valve controlled by said control portion to switch air passages.

* * * * *